United States Patent [19]

Barbanti et al.

[11] Patent Number: 5,436,154
[45] Date of Patent: Jul. 25, 1995

[54] MONOCLONAL ANTIBODIES AGAINST HUMAN TUMOR NECROSIS FACTOR α

[75] Inventors: Elena Barbanti, Cologno Monzese; Marta Ghislieri, Milan; Fabrizio Marcucci, Legnano; Domenico Trizio, Cassina Rizzardi, all of Italy

[73] Assignee: Farmitalia Carlo Erba S.R.L., Milan, Italy

[21] Appl. No.: 806,401

[22] Filed: Dec. 13, 1991

[30] Foreign Application Priority Data

Dec. 28, 1990 [GB] United Kingdom ............... 9028123

[51] Int. Cl.⁶ ................. A61K 39/395; C12N 5/20; C12N 5/12; C07K 15/28
[52] U.S. Cl. ............... 435/240.27; 530/388.24; 530/387.1; 530/388.23; 424/733.1; 424/158.1
[58] Field of Search ........... 530/388.23, 387.1, 388.2; 435/240.27; 424/85.8, 133.1, 158.1

[56] References Cited

U.S. PATENT DOCUMENTS 4,603,106 7/1986 Cerami.

FOREIGN PATENT DOCUMENTS 288088 10/1988 European Pat. Off.
350690 1/1990 European Pat. Off.
355067 2/1990 European Pat. Off.
453898 10/1991 European Pat. Off.
8908460 9/1989 WIPO.
8008460 2/1990 WIPO.

OTHER PUBLICATIONS

Brennan et. al. Lancet 224(1989).
Schall Cell 61:361 (1990).
Smith Science 248:1019 (1990).
Seckinger J. Biol. Chem 265:1531 1990.
Engleman J. Biol. Chem 265:1531 1990.
Mule J. J. et al. J. Exp Men 171 629 1990.
Jacob et al. Nature 331:356 1988.
Peterson Eur J. Imm. 19:1887 (1989).
Ruddle et al. Journal of Experimental Medicine 1193–1200 1990.
Abstract OR37. Barbanti et al. 2nd International Congress on the Immune . . . 1991.
Hahn et al. PNAS 82:3814 1985.
Craig Biochem Biophys 137:847 1986.
Beutler Nature 229:869 1985.
Pennica et al. Nature 312:724 (1984).
Jones et al. Nature 338:225 (1989).
Gray et al. Nature 312:721 1984.
Beutler et al. Nature 320 584 1986.
Oliff et al. Cell 50:555 1987.
Folk et al. PNAS 86:2365 1989.
Pignet et al. J. Exp. Med. 166:1280 1987.
Grau et al. Science 237:1210 1987.
Waldmann, Science vol. 252 Jun. 1991 p. 1657.
Hard, Genes and Cancer 1990 Wiley and Sons.
Brineman Hybridoma vol. 6, No. 5, 1987, 489.
Fenday et al. Hybridoma vol. 6, No. 4, 1987, 359.
Bringman et al. Hybridoma vol. 6 No. 5 1987.
Meager Hybridoma vol. 6(3) 1987:305.
Clark, Wiley and Sons, Experimental Foundation Modern Immunology 1991.
Shimamoto et al. Immunology letters p. 311 1988.
Sheehan et al., J. of Immunology, vol. 142, 3884–3893, No. 11, Jun. 1, 1989 "Generation and Characterization of Hamster Monoclonal Antibodies that Neutralize Murine Tumor Necrosis Factors".

*Primary Examiner*—David L. Lacey
*Assistant Examiner*—Lila Feisee
*Attorney, Agent, or Firm*—Nikaido, Marmelstein, Murray & Oram

[57] ABSTRACT

A monoclonal antibody is provided which is able to neutralize both human TNF α and TNF β, or a binding fragment thereof. A stable hybridoma cell line and progeny thereof are also provided which secrete such a monoclonal antibody. The monoclonal antibody or a fragment thereof may be used to detect the content of human TNF in a sample of body fluid.

5 Claims, 5 Drawing Sheets

MONOCLONAL ANTIBODIES AGAINST HUMAN TUMOR NECROSIS FACTOR α

FIELD OF THE INVENTION

This invention concerns a monoclonal antibody that has high neutralizing activity against human Tumor Necrosis Factor α (TNF α) and neutralizing activity also against human Tumor Necrosis Factor β (TNF β), a hybrid cell line that produces the antibody and the use of the monoclonal antibody.

BACKGROUND OF THE INVENTION

TNF α is a polypeptide of molecular weight 17500, whose primary and tertiary structure has been elucidated (Pennica, D. et al. Nature 312: 724 (1984) and Jones, E. Y. et al. Nature 338: 225 (1989)). TNF α is biologically active as a trimer. The main source of TNF α are cells of the monocyte/macrophage lineage, but after appropriate stimulation it is produced by other cell types as well (e.g. T-lymphocytes).

TNF β is a polypeptide closely related to TNF α. Both molecules show a 28% homology at the amino acid level (see, Pennica, D. et al. Supra and Gray, P. W. et al. Nature 312: 721 (1984)). The main source of TNF β are T-lymphocytes.

TNF α was originally described as a molecule that induces haemorragic necrosis of tumors in mice. However, after large amounts of homogeneous TNF α became available upon cloning of its cDNA, it soon became clear that TNF α mediates a large array of biological activities that allow the definition of TNF α as a mediator of inflammation. See, generally, Beutler, B. and Cerami, A., Nature 320: 584 (1986).

TNF β mediates a qualitatively similar array of biological activities but quantitative differences as to the doses of TNF α or β required to mediate single biological activities have been described.

TNF α plays, within the inflammatory response, a pivotal role in the host defense against invasion of the organism by noxious agents. However, under certain circumstances, like chronic or acute, systemic or localized hyperproduction, TNF α leads, in conjunction with other mediators of the inflammatory response, to a large number of pathologic conditions. Cachexia and septic shock are the best known examples (see, Beutler, B. and Cerami, A., Supra and Oliff, A., et al., Cell 50: 555 (1987). Likewise, TNF α is supposed to play a pathogenic role in AIDS (Folks, T. M., et al., Proc. Natl. Acad. Sci. USA 86: 2365 (1989)), in graft-versus-host disease (Piguet, P. F., et al. J. Exp. Med. 166: 1280 (1987)), in cerebral malaria (Grau, G. E., et al. Science 237: 1210 (1987)), rheumatoid arthritis (Brennan, F. M., et al., Lancet ii: 244 (1989)) and several other disease states.

Much less is known about the in vivo effects of TNF β. Given the fact, however, that it mediates in vitro, biological activities similar to those of TNF α, it can be argued that, in case of hyperproduction, TNF β as well may contribute to the pathogenesis of some disease states.

These results have suggested that antibodies against TNF α and, possibly, also antibodies against TNF β could be therapeutically useful in those disease states in which these polypeptides exert a pathogenic effect.

In order to be therapeutically useful antibodies against TNF α should be able to neutralize the toxic effects of TNF α in vivo. Polyclonal antibodies are easily obtainable from the serum of hyperimmunized animals. These polyclonal antibody preparations, however, are not optimal for in vivo use because

- they are a mixture of antibodies containing antibodies which do not neutralize TNF α,
- they are a mixture of antibodies containing different antibodies having different affinities for the same epitope and
- they are difficult to standardize in terms of potency because of lot-to-lot variations.

Monoclonal antibody technology is the tool of choice to bypass these problems. It permits the in vitro production, under controlled conditions and in unlimited amounts, of monoclonal antibodies of reproducible specificity and affinity against TNF α as against every immunogenic molecule. Clearly, many different monoclonal antibodies can be obtained against one single antigen. They may vary from each other in terms of

- antibody class and subclass,
- epitope specificity,
- binding affinity and
- in vitro and in vivo neutralizing activity.

For therapeutic use it is desirable to employ a monoclonal antibody against TNF α, as against any other antigen, which has high neutralizing activity. This would allow the administration of lower doses of the monoclonal antibody in order to attain therapeutically effective levels in vivo, thus mitigating the possible, undesired side-effects caused by the monoclonal antibody.

BRIEF SUMMARY OF THE INVENTION

In this respect, the present invention provides a novel monoclonal antibody or a binding fragment thereof which is able to neutralize human TNFα. The antibody according to the present invention has high TNFα neutralizing activity both in vitro as well as in vivo. Thus, in vitro, human TNF α exerts half-maximal biological activity at about 0.15 ng/ml ($3.3 \times 10^{-12}$M, assuming TNF α is a trimer). In the presence of 1 μg/ml ($6.25 \times 10^{-9}$M) of said antibody, human TNF α exerts half-maximal biological activity at about 229 ng/ml ($4.6 \times 10^{-9}$M, ratio of half-maximal biological activity in the presence vs absence of 1 μg/ml of said antibody is about 1527). In the presence of 100 ng/ml ($6.25 \times 10^{-10}$M) of said antibody, human TNFα exerts half-maximal biological activity at about 26 ng/ml ($5.2 \times 10^{-10}$M). In the presence of 10 ng/ml ($6.25 \times 10^{-11}$M) of said antibody human TNFα exerts half-maximal biological activity at about 1.9 ng/ml ($3.8 \times 10^{-11}$M). Thus, the monoclonal antibody provided by the present invention is characterized by the fact that it neutralizes in vitro trimeric human TNF α at a ratio lower than about 2:1, in particular at a ratio of about 1.3:1, on a molar basis. In addition, said monoclonal antibody neutralizes and therefore recognizes the structurally related polypeptide human TNF β as well.

Thus, in vitro, human TNF β exerts half-maximal biological activity at about 4 ng/ml ($8 \times 10^{-11}$M, assuming TNF β is a trimer). In the presence of 1 μg/ml ($6.25 \times 10^{-9}$M) of said antibody, human TNF β exerts half-maximal biological activity at about 25.6 ng/ml ($5 \times 10^{-10}$M; ratio of half-maximal biological activity in the presence vs absence of 1 μg/ml of said antibody is about 6.3).

As a second aspect, the present invention shows that said monoclonal antibody is able to precipitate human TNFα as determined by double diffusion in two dimensions (Ouchterlony method). As a third aspect, the present invention shows that the smallest antigen-antibody complex formed upon incubation of said monoclonal antibody with human TNF α is a high molecular weight antigen-antibody complex, containing substantially at least 2 molecules of said monoclonal antibody and at least 1 human TNF α molecule; typically three monoclonal antibody molecules linktogether two molecules of human TNF α.

The term "high molecular weight antigen-antibody complex" is used to denote antigen-antibody complexes of at least 400 kD, typically from about 570 kD to about 600 kD.

Moreover said antibody provides complete protection in mice from an otherwise lethal dose of human TNF α at doses lower than about 1 μg/mouse, typically from about 0.4 to about 0.8 μg/mouse. It has to be noticed that 0.4 μg/mouse correspond to about 20 μg/kg body weight.

The invention further provides a stable hybridoma cell line and progeny thereof which produces such monoclonal antibody.

The invention additionally provides a process for the preparation of such monoclonal antibody.

The invention also provides a pharmaceutical composition comprising such monoclonal antibody which is able to neutralize both human TNF α and human TNF β and a pharmaceutically acceptable carrier and/or diluent.

A further aspect of the present invention is also to provide a method of detecting the content of human TNF α in a body fluid.

An object of the present invention is also to provide antiidio typic antibodies which recognize the human TNF α- and human TNF β- receptors.

The monoclonal antibodies according to the present invention can be of any of the classes of immunoglobulins, such as IgM, IgD, IgE, IgA or subclasses of IgG. The monoclonal antibody may be used intact, or as binding fragments, such as $F_v$, Fab, $F(ab')_2$.

Preferably monoclonal antibodies according to the present invention are of the IgG class.

Particularly preferred monoclonal antibodies according to the present invention are those produced by hybridoma clone 78, as herein described, which are of IgG1 k isotype.

Preferred binding fragments of the monoclonal antibodies according to the present invention are $F_v$, Fab, $F(ab')_2$ fragments of said antibodies.

As stated above the present invention provides a process for the preparation of the monoclonal antibody of the invention or binding fragments thereof, which process comprises culturing a hybridoma cell line or progeny thereof according to the invention and recovering the monoclonal antibody thus produced.

The monoclonal antibodies according to the present invention, or the fragments thereof, can be prepared by immortalizing lymphocytes of the B-cell lineage. Immortalization can be accomplished through transformation with an oncogenic virus or through fusion with an already immortal cell line (e.g. myeloma or lymphoblastoid cell line). The latter approach, which was originally described by Koehler and Milstein (Koehler, G. and Milstein, C., Nature 256: 496 (1975)) gives rise to immortal hybrid cell lines capable of unlimited growth and antibody production. The immortal cell lines thus obtained may be cloned and screened in such a way as to detect antibodies against the desired antigen in the cell supernatants. A large number of screening techniques have been described in the literature and are well-known to those skilled in the art. These techniques unequivocally allow the isolation of monoclonal antibodies against the desired antigen(s). However, if the operator wants to isolate a monoclonal antibody having particular properties (i.e. having high or low affinity for the antigen, being neutralizing or non-neutralizing) the screening techniques have to be set up in such a way as to allow him to isolate monoclonal antibodies having the desired properties. The way these assays are set up depends on the property one is looking for, on the antigen against which the operator wishes to obtain the antibodies and is, generally speaking, not predictable and must be studied on a case by case basis. This step, however, is of crucial importance if the operator wants to isolate monoclonal antibodies with high activity.

If desired, once the cell lines producing the monoclonal antibodies with the desired properties against human TNF α have been isolated according to the present invention, they can be used as a source of the genes encoding the monoclonal antibodies.

These genes can be isolated by preparing first cDNA libraries from messenger RNA. A single cDNA clone, coding for the immunoglobulin is then isolated and may be further manipulated. The ultimate goal of these manipulations is usually, but not exclusively, that of generating antibodies of reduced immunogenicity upon in vivo administration into a host different from the one from which the original antibodies were derived. This can be achieved by ligation of the nucleotides corresponding to the variable region genes of the original species to nucleotides corresponding to the constant region genes of the species to which the antibodies have to be administered. Alternatively, nucleotides encoding the regions of the original monoclonal antibody determining complementariness may be substituted for corresponding nucleotides of the variable regions of antibody genes of the species to which the antibodies have to be administered. Finally, the original or the modified cDNA clone may then be isolated and placed into suitable prokaryotic or eukaryotic expression vectors and subsequently transfected into a host for ultimate bulk production.

In the accompanying tables,

Table 1 shows the parameters of the binding of human TNFα to the monoclonal antibody of the present invention.

Table 2 shows the concentrations of human TNF α giving half-maximal biological activity in the absence or presence of different concentrations of said monoclonal antibody.

Table 3 shows the effect on survival of the administration of different doses of human TNF α into mice.

Table 4 shows the protective effect of the monoclonal antibody of the present invention in mice treated with two lethal doses of TNF α.

Table 5 shows the protective effect of the monoclonal antibody of the present invention injected into mice at different times before and after the treatment with two lethal doses of TNF α.

DETAILED DESCRIPTION OF THE INVENTION

With respect to characterizing the claimed hybrid cell line, the terms "permanent" and "stable" mean viable over a prolonged time, typically at least about six months. The invention enables a stable, permanent hybridoma cell line to be provided which maintains the ability to produce the specified monoclonal antibody through at least 25 passages.

The term "monoclonal antibody" refers to an antibody selected from antibodies whose population is substantially homogeneous, i.e. the individuals of the antibody population are identical except for naturally occurring mutations.

The term "antibody" is also meant to include intact molecules as well as fragments thereof, such as $F_v$, Fab and F(ab')$_2$, which are capable of binding antigen. Fab and F(ab')$_2$ fragments lack the Fc fragment of antibody, clear more rapidly from the circulation and may have less non specific tissue binding than intact antibody. It will be appreciated that $F_v$, Fab, and F(ab')$_2$ and other fragments of the monoclonal antibody of the present invention may be used as well as the intact antibody for the same purposes, e.g. the detection of TNF α and treatment of those disease states in which TNF α has been shown to play a detrimental role.

The term "neutralizing" is used to denote the ability of antibody-containing solutions to block the capacity of TNF α and TNFβ to exert their biological activities in vitro and/or in vivo.

The term "enhanced or high TNF α neutralizing activity in vitro" is used to denote the ability of a solution containing a monoclonal antibody to neutralize human TNF α at a < 6:1 ratio on a weight basis and at a <2:1 ratio on a molar basis at doses of monoclonal antibody ≦10 ng/ml.

The term "enhanced or high TNF α neutralizing activity in vivo" is used to denote the ability of a solution containing a monoclonal antibody to block, at doses of ≦20 μg/kg body weight, the capacity of TNF α to play a detrimental role in vivo.

The monoclonal antibody of the present invention is indeed able to afford complete protection in mice from an otherwise lethal dose of TNF α at doses lower than 1 μg/mouse typically from about 0.4 to about 0.8 μg/mouse. It has to be noted that 0.4 μg/mouse corresponds to about 20 μg/kg body weight.

In a preferred embodiment according to the present invention such a monoclonal antibody is secreted by a hybridoma cell line which has been prepared using cells of an immortalizing cell line and cells derived from a mouse which had been immunized with human recombinant TNF α.

The immortalizing cell line is a cell line which, for practical purposes, can be maintained perpetually in cell culture. In other words, it is stable and permanent and, when fused with cells which do not exhibit these properties, is able to confer the properties on the fusion product.

Any appropriate immortalizing cell line may be used. Typically, a plasmacytoma (myeloma) of mammalian origin may be employed. A preferred type of cell line is a murine hypoxanthine-phosphoribosyl-transferase (HPRT) deficient plasmacytoma. One such cell line is particularly preferred. This is the NSO cell line, a well-known HPRT-deficient plasmacytoma of BALB/c origin which does not produce or secrete either immunoglobulin or heavy or light immunoglobulin chains on its own (Clark, M. R. and Milstein, C. *Somatic Cell Genet.* 7: 657 (1981)).

The immortalizing cells are fused with cells, at least some of which produce antibodies which bind specifically to human TNF α.

The antibody-producing cells are generally obtained from a mouse immunized with respect to human TNF α. Commercially available human TNF α may be used for this purpose. After fusion, the fusion products are screened for those secreting the desired monoclonal antibodies.

In vitro they are first tested in an ELISA that detects antibodies against TNF α. Then they are tested for their ability to neutralize the cytotoxic activity of human TNF α on mouse LM cells.

Progeny of the clones producing the desired monoclonal antibodies can be then grown in vitro in suitable culture media in tissue culture flasks or in a large-scale culture device (e.g. Acusyst, Endotronics, Coon Rapids, Minn.) or in vivo as an ascitic tumor in laboratory animals (e.g. mice or rats).

If desired, the antibody can be separated from the culture medium or the body fluid, as the case may be, by techniques such as ammonium sulfate precipitation, ion exchange chromatography, high-performance liquid chromatography or by other techniques known to those of ordinary skill in the art. According to the present invention monoclonal antibodies with high neutralizing activity against TNF α and neutralizing activity also against TNF β are therefore provided, which are characterized in that:

a) their population is substantially homogeneous, b) they are produced by immortal cells which are themselves hybrids between an immortal cell line and an antibody-producing cell, c) they show enhanced TNF α neutralizing activity in vitro and in vivo, d) they are able to neutralize, thereby recognizing, human TNFβ, e) they precipitate human TNFα,
f) they form with human TNFα, in solution, complexes the smallest of which contain substantially at least 2 monoclonal antibody molecules and have high molecular weight, typically of at least 400 kD.

By virtue of their TNF α and TNF β neutralizing activity the monoclonal antibodies of the present invention can be employed in mammals, including humans for prophylactic and/or therapeutic use in any disease state in which TNF α and/or TNF β are known to exert a pathogenic effect. Typically such disease states ape cachexia, septic shock, graft-versus-host disease, AIDS, cerebral malaria, rheumatoid arthritis, chronic and acute inflammatory diseases, myocardial ischaemia and others in which it is already known or will be known in the future that TNF α and/or TNF β play a detrimental role. The dosage levels suitable for local or systemic administration to adult humans of the monoclonal antibodies according to the present invention, e.g. those produced by hybridoma clone 78, may range from about 20 µg to about 1 mg of antibody per kilogram of body weight. Single or multiple administrations of the compositions can be carried out with dose levels and pattern being selected by the treating physician. In any event, the pharmaceutical formulations should provide an antibody quantity sufficient to effectively treat or prophylactically treat the patient.

The monoclonal antibody of this invention may be formulated either alone or together with other pharmaceutically active agents in pharmaceutical compositions by including appropriate amounts of the monoclonal antibody together with a pharmaceutically acceptable carrier and/or diluent.

Alternatively, a monoclonal antibody of the present invention can be administered in a combined method of treatment with a different pharmaceutically active agent. Pharmaceutically active agents, that can be formulated with the monoclonal antibodies of the present invention, or alternatively can be administered in a combined method of treatment, can be for instance antibodies, in particular monoclonal antibodies, against other antigens, thus providing a "cocktail" containing a monoclonal antibody of the present invention and one or more (monoclonal) antibodies against other antigens involved in the pathogenesis of the relevant disease state.

Further active agents, that can be formulated with the monoclonal antibodies of the present invention, or alternatively can be administered in a combined method of treatment, especially in order to produce a therapeutically useful effect, depend on the disease state to be cured and are, for instance, commercially available gamma globulin and immune globulin products, antibiotics, antimicrobial products, antibacterial and antitumor agents or a mixture of two or more of them.

Moreover the monoclonal antibodies of the present invention can be used alone or in a combined method of treatment with antibacterial and, in particular, with anti-neoplastic agents, so as to prevent or ameliorate the side effects arising therefrom. Typical side effects which can be treated are e.g. cachexia, nausea, vomiting, anorexia, alopecia, diarrhea and neutropenia. Typically, the antimicrobial agents may include a penicillin in conjunction with an aminoglycoside (e.g. gentamycin, tobramycin). However several well known additional agents, e.g. cephalosporins, can be utilized.

The term "antineoplastic agent" is meant to comprise both a single antitumor drug and "cocktails" i.e. a mixture of such drugs, according to the clinical practice. Antitumor agents that can be formulated with a compound of the invention or alternatively, can be administered in a combined method of treatment are e.g. doxorubicin, daunomycin, epirubicin, idarubicin, etoposide, fluorouracil, mephalan, cyclophosphamide, bleomycin, vinblastin and mitomycin or a mixture of two or more thereof.

The term "combined" method of treatment is meant to include both separate and substantially contemporaneous administration of a pharmaceutical composition containing a monoclonal antibody according to the invention and a pharmaceutical composition containing a different pharmaceutically active agent.

Accordingly, a preferred object of the present invention is a combined method of treatment of cancer in mammals, including humans, in need of such treatment, said method comprising administering 1) a monoclonal antibody according to the present invention or a binding fragment thereof, and
2) an antitumor agent, in amounts and close enough together in time sufficient to produce a therapeutically useful effect.

Object of the present invention is also to provide products containing a monoclonal antibody according to the present invention, or a binding fragment thereof and an antitumor agent as a combined preparation for simultaneous, separate or sequential use in anti-cancer therapy.

The monoclonal antibodies of the invention and the binding fragments thereof can therefore be used in a treatment to ameliorate a cancer. They may be administered to a patient suffering from a cancer treatable with an antitumor agent, for example an anthracycline glycoside such as doxorubicin, daunomycin, epirubicin or idarubicin as mentioned above. An antibody according to the invention and an antitumor agent such as anthracycline glycoside can be administered to improve the condition of a patient having a leukaemia such as myeloblastic leukaemia, lymphoma, sarcoma, neuroblastoma, Wilm's tumor or malignant neoplasm of the bladder, breast, lung or thyroid.

Figure 2:
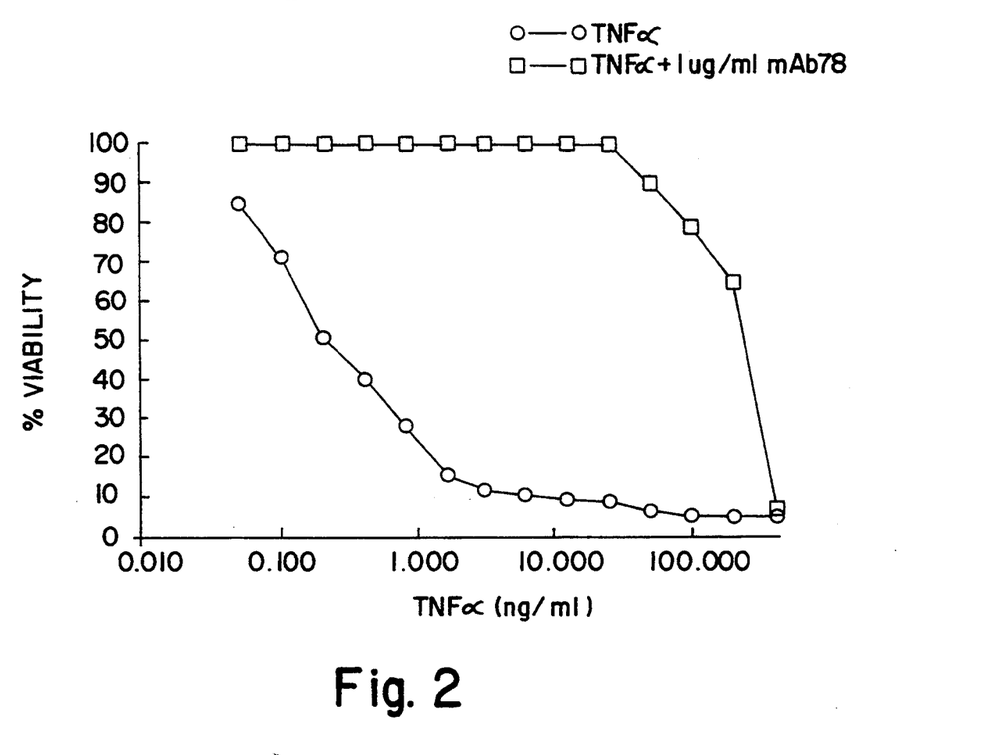
FIG. 2 shows the neutralizing activity of 1 μg/ml ($6.25 \times 10^{-9}$M) of the monoclonal antibody on different doses of human TNF α.

Moreover the high neutralizing activity of the antibody according to the present invention, as shown e.g. in FIG. 2, suggests that said antibody recognizes an epitope close to or within the receptor-binding site of human TNF α. Two TNF α receptors have been characterized (Schall, T. J. et al. Cell 61: 361 (1990) and smith, C. A. et al. Science 248: 1019 (1990)).

Figure 3:
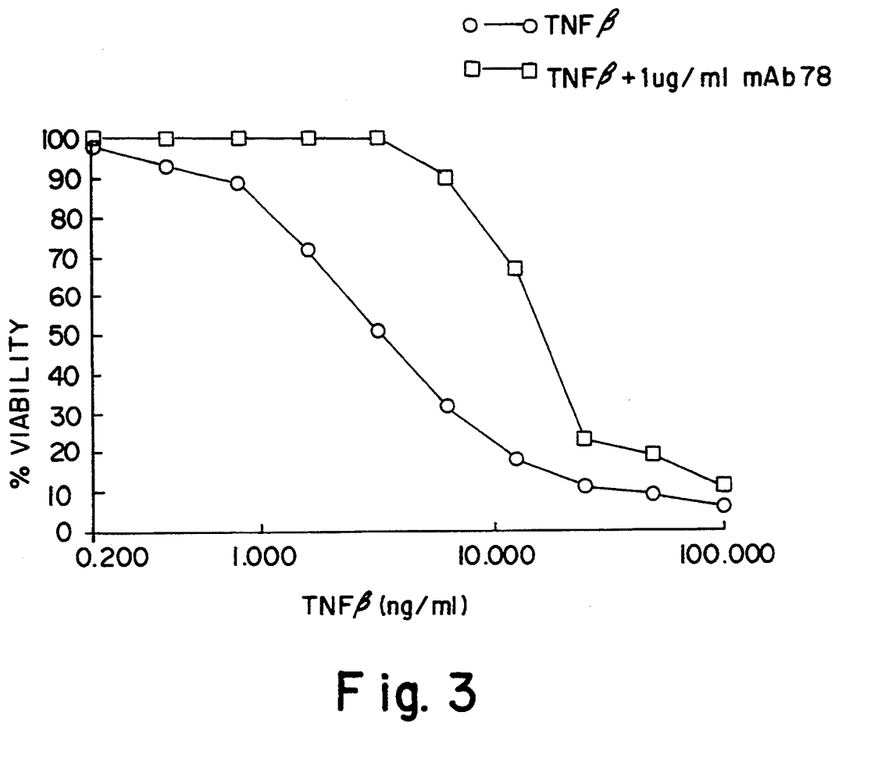
FIG. 3 shows the neutralizing activity of 1 μg/ml of the monoclonal antibody on different doses of human TNF β.

Both receptors bind human TNF α and human TNF β with almost equal affinity when expressed on whole cells. Soluble forms of the two receptors, however, bind human TNF β with much lower affinity than human TNF α (Seckinger, P. et al. *J. Biol. Chem.* 264: 11966 (1989) and Engelmann, H. et al. *J. Biol. Chem.* 265: 1531 (1990)). This result suggests that solubilization of the extracellular domain of the receptors induces a change in the relative affinities for human TNF α and human TNF β. If the monoclonal antibody of the present invention recognizes an epitope within the receptor-binding site of human TNF α then it should functionally behave like a TNF α receptor, i.e. it should recognize both human TNF α as well as human TNF β. Since said monoclonal antibody is a soluble molecule, it should behave functionally like a soluble TNF α receptor, i.e. it should bind human TNF α with a much higher affinity than human TNF β. FIG. 3 shows that this is indeed the case. For human TNF β the ratio of half-maximal biological activity in the presence vs absence of 1 μg/ml of said antibody is 6.3. This suggests that said monoclonal antibody binds to human TNF α and human TNF β like a soluble TNF α receptor. It is therefore ideally suited for being used as an immunogen in order to obtain, according to standard techniques well-known to those skilled in the art (see, generally, Anti-idiotypes, receptors and molecular mimicry, Linthicum, D. S. and Farid, N. R., Eds., Springer-Verlag Heidelberg, 1988) antiidiotypic antibodies which bind to the monoclonal antibody of the present invention like human TNF α. Consequently, these monoclonal antiidiotypic antibodies that are able to bind to TNFα- receptors like TNFα and consequently mimic the biological activities of TNFα can be therapeutically useful in those diseases in which administration of TNFα is likely to play a benefical role. These diseases states are e.g. cancer, in which the antiidiotypic antibodies of the invention, similarly to TNFα, can be administered either alone or, preferably, as part of a combined method of treatment (Mulè, J. J. et al. *J. Exp. Med.* 171: 629 (1990)) and some autoimmune diseases (Jacob O. J. and McDevitt, H. O., *Nature* 331: 356 (1988)).

The monoclonal antibodies and the pharmaceutical compositions, according to the present invention can be administered parenterally by subcutaneous, intramuscular, intraarterial or intravenous administration.

The pharmaceutical compositions containing the monoclonal antibodies of the present invention are usually prepared following conventional methods.

Generally speaking, carriers and/or diluents, according to the pharmaceutical composition of the present invention include alcoholic/aqueous solutions, emulsions, or suspensions, including saline or buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers, such as those based on Ringer's dextrose, and the like. Preservatives and other additives can also be present such as, for example, antimicrobials, antioxidants, chelating agents, inert gases, and the like. See, generally, *Remington's Pharmaceutical Sciences,* 16th Ed., Mack, eds., 1980.

Usually, in disease states in which TNF α exerts a pathogenic effect, TNF α levels in body fluids increase compared to the levels detectable in the same body fluids of healthy individuals. Therefore determination of TNF α levels in these body fluids can be of diagnostic and prognostic value.

A further aspect of the present invention is, therefore, to provide immunoassays where the biological properties of the monoclonal antibodies according to the present invention are particularly advantageous. For the purpose of the present invention, human TNF α which is detected by the monoclonal antibody of the invention may be present in biological fluids or tissue. Any sample, obtained from an individual, containing an unknown amount of human TNF α can be used. Normally, the sample is a liquid, such as, for example, blood, serum, plasma and the like.

The monoclonal antibodies of the present invention are particularly suited for use in immunoassays wherein they may be utilized in liquid phase or bound to a solid phase carrier. In addition, the monoclonal antibody in these immunoassays can be detectably labeled in various ways.

There are many carriers to which the monoclonal antibody of the present invention can be bound and which can be used in detecting the presence of human TNF α. Well-known carriers include glass, polystyrene, polypropylene, polyethylene, dextran, nylon, amylases, natural and modified celluloses, polyacrylamides, agaroses and magnetite. The nature of the carrier can be either soluble to some extent or insoluble for the purposes of the present invention. Those skilled in the art will note many other suitable carriers for binding monoclonal antibody, or will be able to ascertain the same by the use of routine experimentation.

There are many different labels and methods of labeling known to those of ordinary skill in the art. Examples of the types of labels which can be used in the present invention include, but are not limited to, enzymes, radioisotopes, fluorescent compounds, chemiluminescent compounds, bioluminescent compounds and metal chelates. Those of ordinary skill in the art will know of other suitable labels for binding to the monoclonal antibody, or will be able to ascertain the same by the use or routine experimentation. Furthemore, the binding of these labels to the monoclonal antibody can be accomplished using standard techniques commonly known to those of ordinary skill in the art.

One of the ways in which a monoclonal antibody of the present invention can be detectably labeled is by linking the same to an enzyme. This enzyme, in turn, when later exposed to its substrate, will react with the substrate in such a manner as to produce a chemical moiety which can be detected, for example, by spectrophotometric or fluorometric means. Examples of enzymes which can be used to detectably label the monoclonal antibodies of the present invention, include malate dehydrogenase, staphyloccocal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase.

The monoclonal antibody of the present invention can also be labeled with a radioactive isotope which can then be determined by such means as the use of a gammacounter or a scintillation counter. Isotopes which are particularly useful for the purpose of the present invention are: $^3H$, $^{125}I$, $^{131}I$, $^{32}P$, $^{35}S$, $^{14}C$, $^{51}Cr$, $^{36}Cl$, $^{37}Co$, $^{58}Co$, $^{59}Fe$, and $^{75}Se$.

It is also possible to label the monoclonal antibody with a fluorescent compound. When the fluorescently labeled monoclonal antibody is exposed to light of the proper wave length, its presence can then be detected due to the fluorescence of the dye. Among the most commonly used fluorescent labeling compounds are fluorescein isothiocyanate, rhodamine, phycoerythrin, phycocyanin, allophycocyanin, ophthaldehyde and fluorescamine.

The monoclonal antibody of the invention can also be detectably labeled using fluorescent emitting metals such as $^{152}Eu$, or others of the lanthanide series. These metals can be attached to the antibody molecule using such metal chelating groups as diethylenetriaminepentaacetic acid (DTPA) or ethylenediaminetetraacetic acid (EDTA).

The monoclonal antibody of the present invention also can be detectably labeled by coupling it to a chemiluminescent compound. The presence of the chemiluminescent-tagged monoclonal antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the monoclonal antibody of the present invention. Bioluminescence is a type of chemiluminescence found in biological systems in which a catalytic protein increases the efficiency of the chemiluminescent reaction. The presence of a bioluminescent monoclonal antibody is determined by detecting the presence of luminescence. Important bioluminescent compounds for purposes of labeling are luciferin, luciferase and aequorin.

Another technique which may also result in greater sensitivity when used in conjunction with the present invention consists of coupling the monoclonal antibody of the present invention to low molecular weight haptens. The haptens can then be specifically detected by means of a second reaction. For example, it is common to use such haptens as biotin (reacting with avidin) or dinitrophenyl, pyridoxal and fluorescamine (reacting with specific anti-hapten antibodies) in this manner.

The monoclonal antibodies of the present invention are ideally suited for the preparation of a kit. Such a kit may comprise a carrier means being compartmentalized to receive one or more container means such as vials, tubes and the like, in close confinement therewith, each of said container means comprising the separate elements of the immunoassay to be used. A similar kit may be prepared comprising compartmentalized carrier means having one or more container means comprising separate elements suitable for therapeutic use according to the present invention.

The types of immunoassay which can be used or incorporated in kit form are many. Typical examples of some of the immunoassays which can utilize the antibodies of the invention are competitive assays and immunometric, or sandwich, immunoassays.

By the term "immunometric assay" or "sandwich immunoassay", it is meant to include simultaneous sandwich, forward sandwich and reverse sandwich immunoassays. These terms are well understood by those of ordinary skill in the art. Those of ordinary skill in the art will also appreciate that the monoclonal antibody of the present invention may be useful in other variations and forms of immunoassays which are presently known or which may be developed in the future. These are intended to be included within the scope of the present invention.

In a forward sandwich immunoassay, a sample is first incubated with a solid phase immunoabsorbent containing monoclonal antibody against human TNF α. Incubation is continued for a period of time sufficient to allow the antigen in the sample to bind to the immobilized antibody in the solid phase. After the first incubation, the solid phase immunoabsorbent is separated from the incubation mixture and washed to remove excess antigen and other interfering substances, such as non-specific binding proteins, which also may be present in the sample. Solid phase immunoabsorbent containing human TNF α to the immobilized antibody is subsequently incubated for a second time with soluble labeled antibody or antibodies. After the second incubation, another wash is performed to remove unbound labeled antibody(ies) from the solid phase immunoabsorbent and removing non-specifically bound labelled antibody(ies). Labeled antibody(ies) bound to solid phase immunoabsorbent is/are then detected and the amount of labeled antibody detected serves as a direct measure of the amount of antigen present in the original sample. Alternatively, labeled antibody which is not associated with the immunoabsorbent complex can also be detected, in which case the measure is in inverse proportion to the amount of antigen present in the sample. Forward sandwich assays are described, for example, in U.S. Pat. Nos. 3,867,517; 4,012,294 and 4,376,110.

In carrying out forward immunometric assays, the process comprises, in more detail:
  (a) first forming a mixture of the sample with the solid phase bound antibody and incubating the mixture for a time and under conditions sufficient to allow antigen in the sample to bind to the solid phase bound antibody.
  (b) after said incubation of step (a), adding to the mixture the detectably labeled antibody or antibodies and incubating the new resultant mixture for a period of time and under conditions, which are sufficient to allow the labeled antibody to bind to the solid phase immunoabsorbent;
  (c) separating the solid phase immunoabsorbent from the mixture after the incubation in step (b); and
  (d) detecting either the labeled antibody or antibodies bound to the solid phase immunoabsorbent or detecting the antibody not associated therewith.

In a reverse sandwich assay, the sample is initially incubated with labeled antibody, after which the solid phase immunoabsorbent containing multiple immobilized antibodies is added thereto, and a second incubation is carried out. The initial washing step of a forward sandwich assay is not required, although a wash is performed after the second incubation. Reverse sandwich assays have been described, for example, in U.S. Pat. Nos. 4,098,876 and 4,376,110.

In carrying out reverse immunometric assays, the process comprises, in more detail:
  (a) first forming a mixture of the sample with the soluble detectably labeled antibody for a period of time and under conditions, which are sufficient to allow antigen in the sample to bind to the labeled antibody;
  (b) after the incubation of step (a), adding to the mixture the solid phase bound antibodies and incubating the new resulting mixture for a period of time and under conditions sufficient to allow antigen bound to the labeled antibody to bind to the solid phase antibodies;
  (c) separating the solid phase immunoabsorbent from the incubating mixture after the incubation in step (b); and
  (d) detecting either the labeled antibody bound to the solid phase immunoabsorbent or detecting the labeled antibody not associated therewith.

In a simultaneous sandwich assay, the sample, the immunoabsorbent having multiple immobilized antibodies thereon and labeled soluble antibody or antibodies are incubated simultaneously in one incubation step. The simultaneous assay requires only a single incubation and has a lack of washing steps. The use of a simultaneous assay is by far the preferred method. This type of assay brings about ease of handling, homogeneity, reproducibility, linearity of the assays and high precision. The sample containing antigen, solid phase immunoabsorbent with immobilized antibodies and labeled soluble antibody or antibodies is incubated under conditions and for a period of time, which are sufficient to allow antigen to bind to the immobilized antibodies and to the soluble antibody. In general, it is desirable to provide incubation conditions sufficient to bind as much antigen as possible, since this maximizes the binding of labeled antibody to the solid phase, thereby increasing the signal. Typical conditions of time and temperature are two hours at about 45° C., or twelve hours at about 37° C.

Antigen typically binds to labeled antibody more rapidly than to immobilized antibody, since the former is in solution whereas the latter is bound to the solid phase support. Because of this, labeled antibody may be employed in a lower concentration than immobilized antibody, and it is also preferable to employ a high specific activity for the labeled antibody. For example, a labeled antibody according to this invention can be employed at a concentration of about 1–50 ng/per assay, whereas immobilized antibody can have a concentration of 10–500 ng/per assay per antibody. Where radiolabeled, the antibody might have a specific activity with, for instance, one radioiodine per molecule, or as high as two or more radioiodines per molecule of antibody.

In carrying out the simultaneous immunometric assay on a sample containing a multivalent antigen, the process comprises, in more detail:

(a) simultaneously forming a mixture comprising the sample, together with the solid phase bound antibody and the soluble labeled antibody or antibodies;

(b) incubating the mixture formed in step (a) for a period of time and under conditions sufficient to allow antigen in the sample to bind to both immobilized and labeled antibodies;

(c) separating the solid phase immunoabsorbent from the incubation mixture after the incubation; and (d) detecting either labeled antibody bound to the solid phase immunoabsorbent or detecting labeled antibody not associated therewith.

Of course, the specific concentrations of labeled and immobilized antibodies, the temperature and time of incubation as well as other assay conditions can be varied depending on various factors, including the concentration of antigen in the sample, the nature of the sample, and the like. Those skilled in the art will be able to determine operative and optimal assay conditions for each determination by employing routine experimentation.

After the incubation, the solid phase immunoabsorbent is removed from the incubation mixture. This can be accomplished by any of the known separation techniques, such as sedimentation and centrifugation. Detection can be performed by a scintillation counter, for example, if the label is a radioactive gamma-emitter, or by a fluorometer, for example, if the label is a fluorescent material. In the case of an enzyme label, the detection can be accomplished by colorimetric methods which employ a substrate for the enzyme.

Other steps such as washing, stirring, shaking, filtering and the like may of course be added to the assays, as is the custom or necessity for any particular situation.

There are many solid phase immunoabsorbents which have been employed and which can be used in the present invention. Well known immunoabsorbents include beads formed from glass, polystyrene, polypropylene, dextran, nylon and other materials and tubes formed from or coated with such materials and the like. The immobilized antibodies can be either covalently or physically bound to the solid phase immunoabsorbent, by techniques such as covalent binding via an amide or ester linkage, or by absorption. Those skilled in the art will know many other suitable solid phase immunoabsorbents and methods for immobilizing antibodies thereon, or will be able to ascertain such, using no more than routine experimentation.

The various aspects of the invention are further described by the following example. This example is not intended to limit the invention in any manner.

EXAMPLE

1. Immunization of mice with human TNF α

Human TNF α (Esquire Chemie AG, Zuerich, Switzerland), diluted in phosphate-buffered saline (PBS) supplemented with complete Freund's adjuvant (CFA, Difco, Detroit, Mich., 500 μl to 500 μl PBS), is administered into the rear foot-pads of 5 BALB/c mice at a dose of 30 μg/mouse. 14 days after the first immunization human TNF α, diluted in PBS supplemented with CFA as above, is administered subcutaneously to the same mice at a dose of 30 μg/mouse. 14 days after the second immunization human TNF α, diluted in PBS, is administered intraperitoneally to the same mice at a dose of 30 μg/mouse. 14 days after the third immunization human TNF α is administered to the same mice at the same doses and on the same conditions as for the third immunization. After 3 days the mouse that has the highest titer of antiTNF α antibodies in the serum as determined in an ELISA is sacrified.

2. Immortalization of mouse spleen cells producing anti-TNFα antibodies.

The spleen is removed aseptically, homogenized and the resulting cell suspension centrifuged. At the same time NSO myeloma cells (>99% viable cells) are centrifuged as well. Both pellets are then resuspended in complete RPMI medium. Complete RPMI medium is RPMI 1640 (Flow, Opera, Italy) supplemented with 1 mM sodium pyruvate (Gibco, Paisley, Scotland), nonessential amino acids (Gibco), 100 μg/ml of streptomycin, 1.5 μg/ml of amphotericin B and additional glutamine (2 mM). Both cell suspensions are combined at a spleen cell: myeloma cell ratio of 10:1. The resulting cell mixture is centrifuged for 10 min at 400 g. The medium is discarded and 1 ml of polyethylene glycol (PEG 1500, Serva, Heidelberg, West Germany, 40% w/v in complete RPMI medium) is carefully added drop by drop over a 1 minute period in order to allow fusion to take place. 5 ml of complete RPMI medium are then added over a 5 min period, then 10 ml over a 5 min period and finally 15 ml over a 5 min period. The final suspension is centrifuged for 10 min at 400 g and the pellet resuspended in complete RPMI medium supplemented with 20% fetal calf serum (FCS, Flow, heat inactivated at 56° C. for 30 min) so to have a final cell density of $5 \times 10^5$ cells/ml (spleen cells+NSO cells). 200 μl of this suspension are seeded into each well of 96-well tissue culture plates (Falcon No. 3072, Becton Dickinson, Milan, Italy) that have been previously seeded with irradiated mouse peritoneal cells (3000 Rad; $2.5 \times 10^4$ cells/well). Plates containing the fusion products are then incubated for 24 hours at 37° C., 5% $CO_2$. Then 50 μl of complete RPMI medium supplemented with 20% FCS and hypoxanthine, aminopterin and thymidine (HAT, respectively $10^{-4}$M, $4 \times 10^{-7}$M and $1.6 \times 10^{-5}$M final concentrations in the plate) are added. In this culture medium only hybridomas can survive, since NSO cells are killed in the presence of aminopterin and unfused spleen cells have a limited lifespan.

The plates are then further incubated at 37° C., 5% $CO_2$. Cultures are fed every 2 days with fresh medium. Growing hybrids are visible by the $4^{th}$ day. Aminopterin is removed from the medium after 3 weeks, and complete RPMI medium supplemented with 20% FCS is used starting from the $5^{th}$ week.

After 10-14 days, cultures are tested for the production of antibodies binding to human TNF α in an enzyme-linked immunosorbent assay (ELISA) and of antibodies neutralizing one of the several biological activities of human TNF α. Typically, because of its ease, the supernatants are tested for their ability to neutralize the cytotoxic activity of human TNF α on mouse LM cells (for a detailed description of the assays, see below). Hybrid cells producing the antibodies with the strongest neutralizing activity are cloned by limiting dilution at an input of 0.5 cells/well of 96-well plates (Falcon) previously seeded with irradiated mouse peritoneal cells (3000 Rad; $2.5 \times 10^4$ cells/well). After 2 weeks growth-positive wells are tested for the production of TNF α-specific antibodies by means of the two assays mentioned above.

One clone, producing antibodies with the strongest neutralizing activity, is selected and further expanded. The supernatant of this clone is tested in order to quantify exactly its neutralizing activity in vitro and in vivo. For this purpose, the immunoglobulin content of the supernatant is first determined in a quantitative ELISA (for a detailed description of the assay, see below). In order to quantify exactly its neutralizing activity in vitro, 1 μg/ml, 100 ng/ml or 10 ng/ml ($6.25 \times 10^{-9}$M, $6.25 \times 10^{-10}$M or $6.25 \times 10^{-11}$M) of the monoclonal antibody are coincubated with increasing doses of human TNF α. After 2 hours the residual cytotoxic activity of human TNF α on mouse LM cells is determined.

In order to see if the monoclonal antibody crossreacts with the closely related polypeptide TNF β, 1 μg/ml of the monoclonal antibody is coincubated with increasing doses of human TNF β and after 2 hours the residual cytotoxic activity of human TNF β on LM cells is determined.

In order to quantify exactly its neutralizing activity in vivo different doses of the monoclonal antibody are then tested for their ability to protect mice from a lethal shock syndrome induced by TNF α coadministered with D-galactosamine (for a detailed description of the assay, see below).

The cells of the hybridoma clone are cloned again as described above in order to assure stability and homogeneity of the cell population. One clone (clone 78) is selected and expanded for further characterization. The monoclonal antibody produced by this clone is found to have heavy chains of the IgG1 subclass and light chains of the k class.

3. Verification of the specificity of a human TNF α-specific monoclonal antibody.

Figure 1:
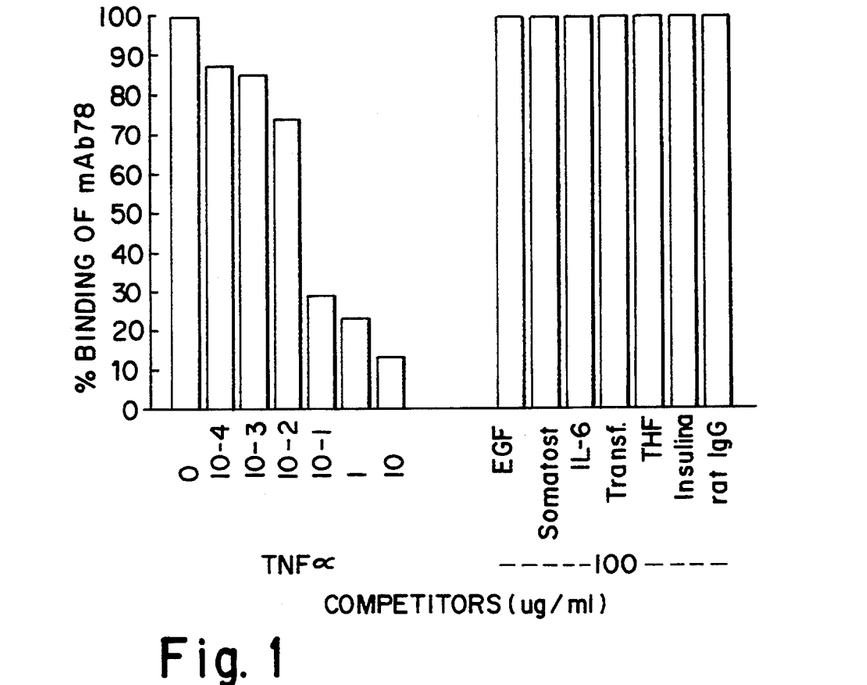
FIG. 1 shows the specificity for human TNF α of the monoclonal antibody, as determined in an ELISA that measures the residual binding to TNF α of 100 ng/ml of the antibody upon incubation with different doses of human TNF α or with different doses of unrelated antigens.

FIG. 1 shows that the binding to human TNF α of the monoclonal antibody produced by hybridoma 78 is displaced only after preincubation with human TNF α but not with a series of unrelated antigens. The unrelated antigens are epidermal growth factor (EGF), somatostatin, interleukin 6 (IL6), transferrin, thymic hormone factor (THF), insulin, rat immunoglobulin G antibodies.

4. In vitro neutralizing activity of a monoclonal antibody with enhanced TNF α neutralizing activity and TNF β neutralizing activity.

FIG. 2 shows the neutralizing activity of 1 μg/ml ($6.25 \times 10^{-9}$M) of the monoclonal antibody produced by hybridoma clone 78 on increasing doses of human TNF α. As can be seen human TNF α alone exerts 50% cytotoxicity at 0.15 ng/ml ($3.3 \times 10^{-12}$M). In the presence of 1 μg/ml of said monoclonal antibody human TNF α exerts 50% cytotoxicity at about 229 ng/ml ($4.6 \times 10^{-9}$M). This shows that 1 μg/ml of said monoclonal antibody completely neutralizes about 228 ng/ml of human TNF α. The ratio of half-maximal biological activity in the presence vs absence of 1 μg/ml of said antibody is therefore about 1527.

Assuming that human TNF α is present in solution as a trimer, it can be deduced that the monoclonal antibody neutralizes human TNF α at a ratio of about 1.3:1 on a molar basis.

FIG. 3 shows that for human TNFβ the ratio of half-maximal biological activity in the presence vs absence of 1 μg/ml of the said antibody according to the invention is about 6.3. Table 2 shows the doses of human TNF α giving 50% cytotoxic activity on LM cells in the absence or in the presence of $6.25 \times 10^{-9}$M, $6.25 \times 10^{-10}$M or $6.25 \times 10^{-11}$M of said antibody. As can be seen, said antibody neutralizes, at all doses tested, human TNF α at a ratio <2 on a molar basis.

5. Affinity of a monoclonal antibody with enhanced TNF α neutralizing activity.

The affinity of the monoclonal antibody according to the present invention is determined by Scatchard analysis. For this purpose, 1 ng/ml ($6.25 \times 10^{-12}$M) of said monoclonal antibody is incubated with different doses of iodinated human TNF α and the amount of antibody-bound human TNFα is thereafter determined.

Figure 4:
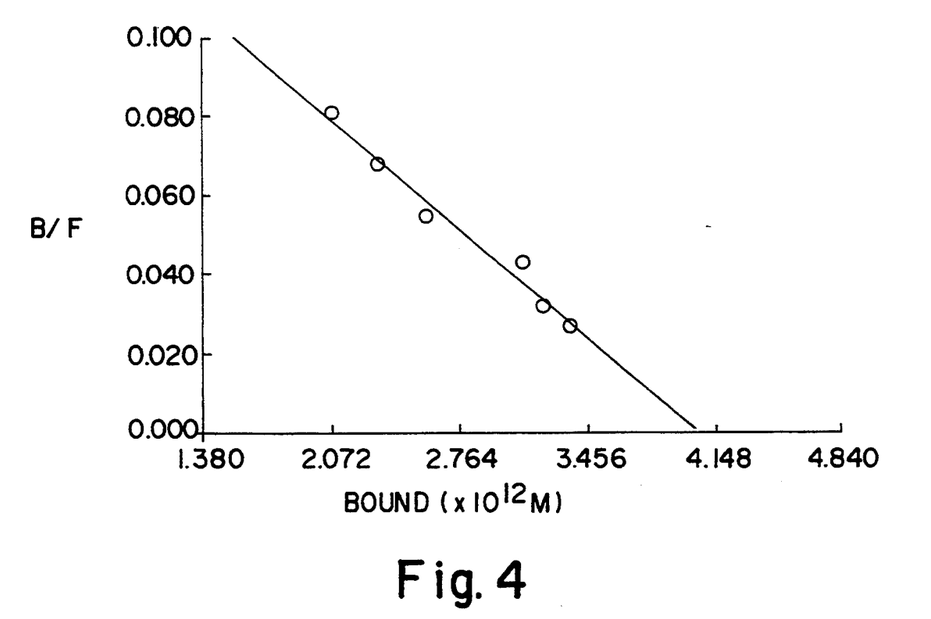
FIG. 4 shows a Scatchard plot of the binding of human TNFα to said monoclonal antibody.

As can be seen from FIG. 4, Scatchard plots of the binding data yield a straight line. Table 1 shows the parameters of human TNF α binding to said monoclonal antibody. As can be seen, the affinity constant ($K_{obs}$) is $3.16 \times 10^{10}$M$^{-1}$ and the highest amount of iodinated human TNF α bindable by $6.25 \times 10^{-12}$M of said monoclonal antibody is $4.34 \times 10^{-12}$M.

6. Dissociation of human TNF α from a monoclonal antibody with enhanced TNF α neutralizing activity.

Figure 5:
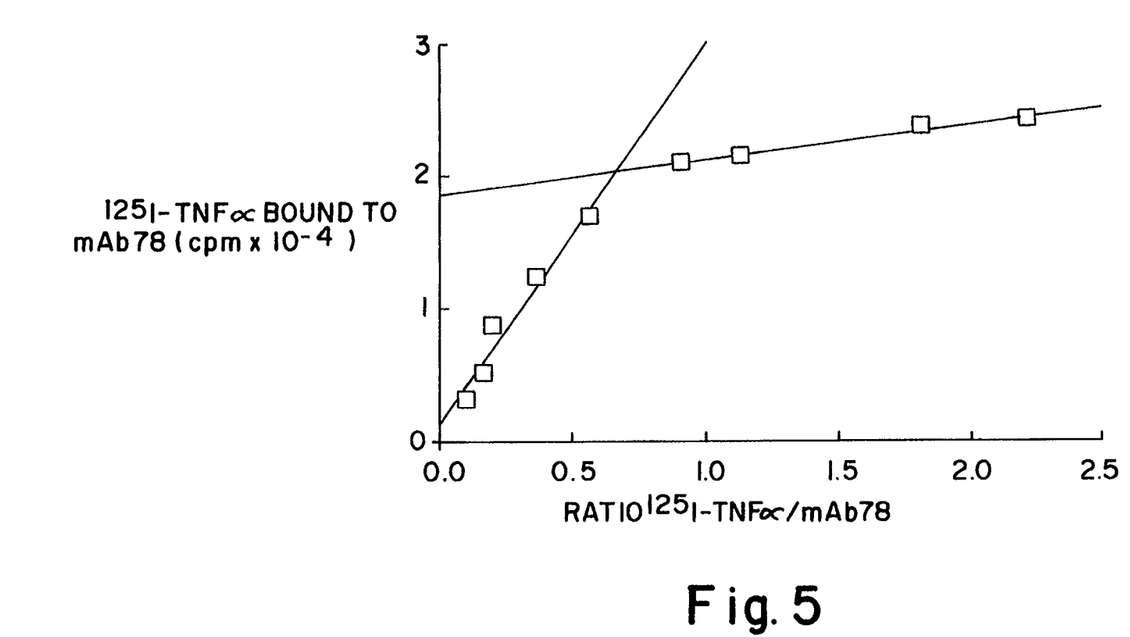
FIG. 5 shows the dissociation of human TNF α from the monoclonal antibody of the present invention.

Dissociation of human TNF α from said antibody is determined by preincubating iodinated human TNF α (2.5 ng/ml, $5 \times 10^{-11}$M) with the monoclonal antibody (2 ng/ml, $1.25 \times 10^{-11}$M) and then measuring dissociation by adding excess unlabelled human TNF α to prevent reassociation of iodinated human TNF α. FIG. 5 shows the result of such an experiment. As can be seen, the dissociation of iodinated human TNF α follows the kinetics of a first order reaction by giving a staight-line plot. The $k_{-1}$ value (dissociation rate constant) determined from this plot is $1.37 \times 10^{-5}$ sec$^1$ (T$\frac{1}{2}$=14 h).

7. Ouchterlony double immunodiffusion in agar.

Figure 6:
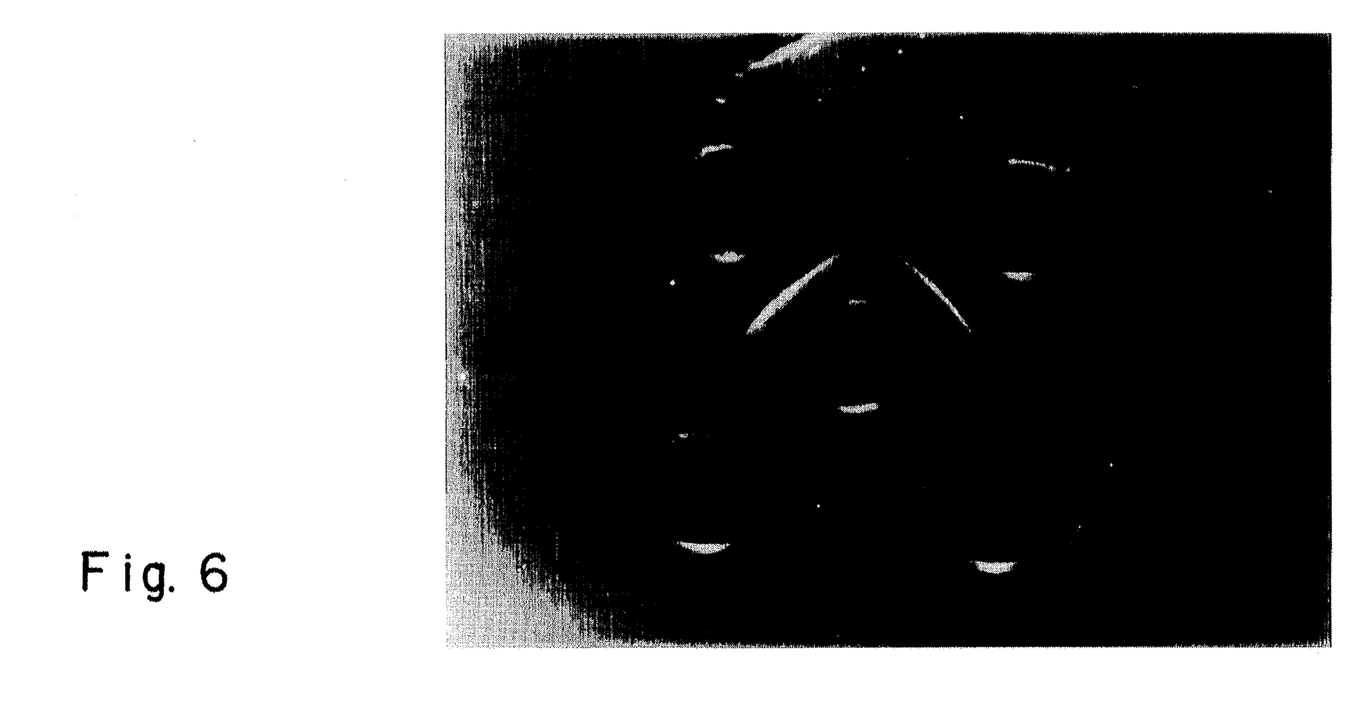
FIG. 6 shows an Ouchterlony double immunodiffusion in agar. In the central trough were added 20 μg of the monoclonal antibody; in the upper left, upper right, lower left and lower right troughs 10 μg, 5 μg, 1.25 μg and 2.5 μg of human TNFα, respectively.

FIG. 6 shows that the monoclonal antibody according to the present invention is able to immunoprecipitate human TNF α. Precipitin bands are formed when 20 μg of said monoclonal antibody (central trough) are allowed to react with 10 μg (upper left trough), 5 μg (upper right) and 2.5 μg (lower right) of human TNF α. At 1.25 μg (lower left trough) of human TNFα the precipitin band is no longer visible. It is known that for an antigen to be precipitated by a monospecific antibody like the one disclosed in the present invention, it must be multivalent and express a minimum of 3 identical epitopes on the same molecule (Sachs, D. H., et al. *J. Immunol.* 109: 1300, 1972). Human TNF α has been described to be a trimer in solution (Jones, E. Y. et al. *Supra*), but there are also reports claiming that in solution human TNF α exists as a dimer (Petersen, C. M., et al. *Eur. J. Immunol.* 19: 1887, 1989). The result of FIG. 6 shows that, by means of the monoclonal antibody of the present invention, it is possible to unambiguously define human TNFα as a trimer.

8. Fast-pressure liquid chromatography (FPLC) size exclusion profiles of mixtures of human TNF α and a monoclonal antibody with enhanced TNF α neutralizing activity.

Figure 7A:
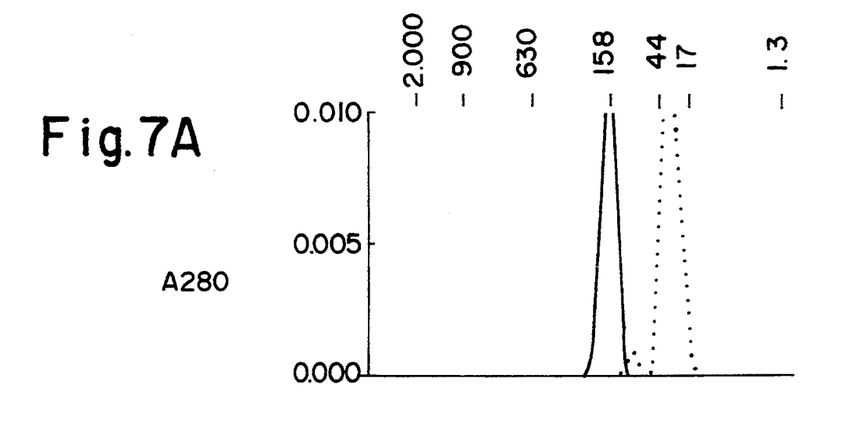
FIGS. 7A–C show the fast-pressure liquid chromatography (FPLC) size exclusion profiles of $2 \times 10^{-6}$M human TNF α alone (- - - FIG. 7A), of $6.25 \times 10^{-6}$M of said monoclonal antibody alone (—FIG. 7A), of a mixture of $2 \times 10^{-6}$M human TNF α and $2 \times 10^{-7}$M of the monoclonal antibody (FIG. 7B) and of a mixture of $10^{-10}$M iodinated human TNF α and $1.25 \times 10^{-11}$M of the monoclonal antibody (FIG. 7C).
Figure 7B:
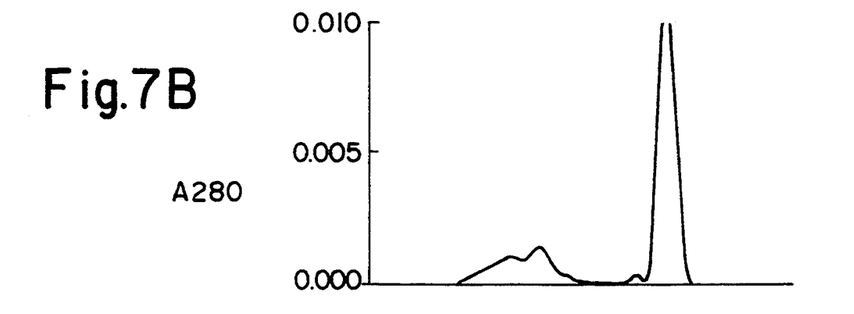
Figure 7C:
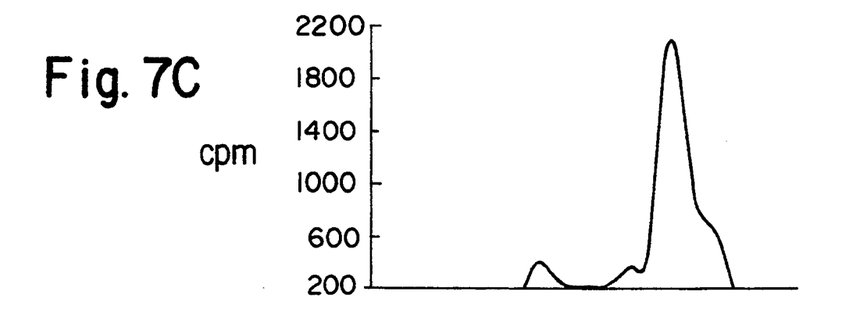

FIGS. 7A–C show the FPLC size exclusion profiles of 100 μg/ml ($2\times10^{-6}$M) human TNF α alone (- - - FIG. 7A), of 100 μg/ml ($6.25\times10^{-6}$M) of said monoclonal antibody alone (—FIG. 7A), of a mixture of 100 μg/ml ($2\times10^{-6}$M) human TNF α and 30 μg/ml ($2\times10^{-6}$M) of the monoclonal antibody (FIG. 7B) and of a mixture of 5 ng/ml ($10^{-10}$M) iodinated human TNF α and 2 ng/ml ($1.3\times10^{-11}$M) of the monoclonal antibody (FIG. 7C). As can be seen human TNF α alone elutes at a volume corresponding to 40 kD. This chromatographic behavior of human TNF α is in agreement with other studies where oligomeric TNF α has been reported to exhibit an apparent molecular weight of 34–40 kD in gel-filtration (Kumitani, M. G., et al. *J. Chromatogr.* 443: 205 (1988)). On the other hand mixtures of human TNF α and the monoclonal antibody set up at reagent concentrations either in large excess of or close to the calculated $K_{obs}$ give rise to complexes that elute at a volume corresponding to a molecular weight of at least 400 kD, typically 570–600 kD (FIG. 7B and 7C).

9. Conclusion drawn from in vitro experiments performed with a monoclonal antibody with enhanced TNF α neutralizing activity.

Considering the molecular weight of the complexes (570–600 kD) formed upon interaction of human TNF α with said monoclonal antibody in view of the fact that the highest amount of human TNF α bindable and neutralizable by the monoclonal antibody is ≈0.7 moles TNF α/mole antibody, it can be concluded that each of said complexes is a high molecular weight complex consisting substantially of at least 2 molecules of said monoclonal antibody and 1 human TNF α molecule, typically 3 molecules of said monoclonal antibody (6 binding arms) linking together 2 molecules of human TNF α (6 epitopes).

Such complexes would be expected to elute, in gel-filtration, at a volume corresponding to 560–580 kD, a value very close to the one observed. Since the results on binding stoichiometry were obtained from experiments performed in antigen excess we exclude that the human TNF α/monoclonal antibody complexes consist of alternating mAb78—huTNFα molecules in an open-chain configuration. Instead, we propose that human TNF α/monoclonal antibody molecules combine to form ring-like structures. The energetic advantage and, consequently, the extreme stability of ring-like antigen—antibody complexes has been discussed and thoroughly studied in divalent hapten—antibody systems (Archer, B. G., and Krakaur, H. *Biochemistry* 16: 618 (1977); Erickson, J. W. et al. *Biochemistry* 30: 2357 (1991); Posner, R. G. et al. *Biochemistry* 30: 2348 (1991) and Dembo, M. and Goldstein, B., *Immunochemistry* 15: 307 (1978)). In fact, dissociation studies (FIG. 5) show that the human TNFα/monoclonal antibody complexes are, indeed, very stable ($K_{-1}=1.37\times10^{-5}$ $\sec^{-1}$). Such values are in the same order of magnitude of those reported for monoclonal antibodies binding to cell-surface antigens according to a monogamous bivalent mode of binding (Mason, D. W. and Williams, A. F., *Biochem. J.* 187: 1 (1989)), another kind of antigen—antibody interaction leading to the formation of similarly stable complexes. Moreover, if, through formation of such cyclic complexes, human TNF α and said monoclonal antibody are allowed to relax into the state of greatest stability, then this explains the apparently paradoxic result that, in antigen excess, the smallest antigen—antibody complex formed is in antibody excess.

In view of such a model, however, the question arises on how human TNF α and said monoclonal antibody can undergo precipitation. Given that in the described complexes no human TNF α epitopes remain free to interact with said monoclonal antibody molecules, we exclude that precipitation results from cross-linking of such complexes. Rather, we favor the possibility that formation of precipitating and cyclic complexes are 2 fundamentally different phenomena in competition with each other. At antigen excess and at low (close to the $K_{obs}$) reagent concentrations formation of cyclic complexes would predominate, at equivalence/antibody excess and at high reagent concentrations formation of complexes built up of alternating antibody—antigen molecules according to classic lattice theory.

Finally, monoclonal antibodies binding to human TNF α like the one described in the present invention may be of advantage in view of possible therapeutic applications in human TNF α—related disease states.

In fact, complexes consisting of at least 2, typically 3 monoclonal antibody molecules can be viewed as microaggregates. Cells of the monocyte—macrophage lineage should preferentially eliminate them from the circulation thereby preventing their deposition in critical organs (e.g. the kidney) and, thus, avoiding immune complex—mediated inflammatory reactions in these districts.

10. In vivo neutralizing activity of a monoclonal antibody with enhanced TNF α neutralizing activity.

In order to evaluate the in vivo neutralizing activity, a model system is used in which mice are injected intraperitoneally with 36 mg D-galactosamine (Fluka AG, Buchs, Switzerland) and human TNF α. D-galactosamine renders the animals extremely susceptible to the lethal effects of human TNF α. As can be seen from Tables 2, 3 and 4, a dose of human TNF α as low as 0.1 μg/mouse kills most of the mice. In fact the administration of such an amount of TNF α to mice will give rise to TNF α levels in the blood close to those that have been detected in humans in disease states in which TNF α has been suggested to play a detrimental role (see Cannon, J. G. et al. *The Journal of Infectious Diseases* 161: 79 (1990)). This model system is therefore suitable for the determination of those doses of an anti-TNF α monoclonal antibody that will be neutralizing in humans in disease states in which TNF α exerts a pathogenic effect.

Tables 3 and 4 show the results of the in vivo protection studies that have been performed with the monoclonal antibody according to the present invention produced by hybridoma clone 78.

Table 3 in particular shows that 0.4 μg/mouse of the monoclonal antibody are able to fully protect mice from the lethal effects of 0.1 μg/mouse of human TNF α coadministered with 36 mg of D-galactosamine. Employing a supralethal dose of 1 μg/mouse human TNF α, 4 μg/mouse of the monoclonal antibody fully protect mice.

Table 4 shows the results of time kinetic studies. As can be seen 10 μg/mouse of the monoclonal antibody are able to fully protect mice from the lethal effects of 1 μg/mouse of TNF α either administered 1 hour and half prior to/or simultaneously with TNF α. If administered 20 minutes after TNF α, partial protection is still observed. On the other hand 1 μg/mouse of the monoclonal antibody fully protects mice if administered up to 40 minutes after 0.1 μg/mouse of TNF α. If administered 2 hours after TNF α, partial protection is still observed. Cells of the hybridoma clone 78 have been deposited in the European Collection of Animal Cell Culture, PHLS Centre for Applied Microbiology & Research, Porton Down, Salisbury, Wilts. SP4 OJG, U.K., with the provisional ECACC accession number 90110707, on Nov. 7, 1990.

METHODS

1. ELISA for the detection of human TNF α-specific antibodies.

Flat bottom microtiter plates (Falcon No. 3912) are coated at 100 μl/well with 1 μg/ml of human TNF α diluted in 100 mM bicarbonate buffer, pH 9.6. After an overnight incubation at 4° C., unabsorbed TNF α is discarded and PBS supplemented with 1% bovine serum albumin (BSA, Armour, Kankakee, Ill.) is added to each well to saturate unoccupied plastic sites.

The plates are further incubated for 3 hours at room temperature. Thereafter plates are washed 3 times with washing buffer (WB), that is PBS supplemented with 0.1% Tween 20 (Merck, Schuchardt, Hohenbrunn, FRG) and 0.01% merthiolate (BDH, Pool, GB). 50 μl of hybridoma supernatants, diluted 1:5 in PBS supplemented with 1% BSA are added to each well, the plates incubated for 60 minutes at 37° C., and washed as above. Then 100 μl of peroxidase-conjugated goat-anti mouse immunoglobulin G (HRPaIgG, BioRad, Richmond, Calif.) diluted 1:3000 in WB are added to each well, the plates are incubated for 45 minutes at 37° C. and washed as above. Then, 100 μl of peroxidase substrate (OPD2, Chemicon, SCI, Rome, Italy, 1 tablet dissolved in 5 ml citrate buffer, OPD4, Chemicon) are added to each well. The reaction is allowed to proceed for 2 minutes at room temperature, after which color development is stopped by the addition of 100 μl/well of 4M $H_2SO_4$. The extent of color development is read on a plate ELISA reader at 492 nm. Supernatants giving optical density (OD) values $>0.5$ are considered positive for the presence of anti-TNF α antibodies.

2. Competitive ELISA for the verification of the specificity of human TNF α-specific antibodies.

100 ng/ml of a hybridoma supernatant are coincubated with different concentrations of human TNF α or with different concentrations of unrelated antigens or with diluent alone (PBS supplemented with 1% BSA) for 2 hours at 37° C. At the end of the incubation period residual TNF α-binding is measured in the previously described ELISA that allows the detection of human TNF α-specific antibodies.

3. ELISA for the quantitative determination of mouse IqG antibodies.

Flat-bottom microtiter plates are coated at 100 μl/well with goat-anti mouse Ig (Organon Teknika, Turnhout, Belgium, 1 μg/well final concentration) diluted in 40 mM phosphate buffer (pH 7.4). After an overnight incubation at 4° C., unabsorbed antibody is discarded and PBS supplemented with 1% BSA is added to each well to saturate unoccupied plastic sites.

The plates are further incubated for 3 hours at room temperature and thereafter washed 3 times with WB. During this incubation period serial two-fold dilutions of a reference mouse IgG preparation (Pel-Freez, Rogers, Ark.) are set up, typically from 5 to 0.25 μg IgG/ml. In parallel, serial two-fold dilutions of supernatants containing an unknown quantity of IgG are set up, typically from 1:100 to 1:12800. All dilutions are performed in PBS supplemented with 1% BSA. 50 μl of each dilution are added to a well, the plates incubated for 60 minutes at 37° C. and then washed as above.

Peroxidase substrate addition and color development is as for 1.

IgG concentrations in the supernatants containing an unknown quantity of IgG are calculated processing the data with an ELISA-SOFT-PC program (Perkin-Elmer, Norwalk, Conn.).

4. ELISA for the typing of heavy and light chains of monoclonal antibodies.

For this purpose a HYBRIDOMA SUB ISOTYPING KIT (Calbiochem, La Jolla, Calif.) is used according to the manufacturer's instructions. Typing is performed on hybridoma supernatants diluted 1:5 in PBS supplemented with 1% BSA. Wells giving OD values $>0.4$ are considered positive for the presence of a monoclonal antibody of a given Ig class, subclass and light chain.

5. Determination of the neutralizing activity in vitro of anti-TNF α monoclonal antibodies.

On day 0 logarithmically growing mouse LM cells (Rubin, B. Y. et al, *J. Exp. Med.* 162: 1099 (1985)) are trypsinized, centrifuged and resuspended at a final concentration of $3 \times 10^5$ cells/ml of Eagle's minimum essential medium supplemented with 5% FCS and 1% glutamine (complete MEM).

100 μl of this suspension are added to the wells of flat bottom microtiter plates (Falcon 3072). Then dilutions of human TNF α or human TNF β (Omnia Res, Cinisello Balsamo, Italy) are set up in complete MEM so to have final concentrations, after addition to the wells, of 1 μg/ml to 25 pg/ml.

Antibody-containing supernatants or solutions are diluted in complete MEM so to have a final concentration, after addition to the wells, of 1 μg/ml, 100 ng/ml or 10 ng/ml monoclonal antibody.

50 μl of each TNF α or TNF β dilution are coincubated with 50 μl of monoclonal antibody or with 50 μl complete MEM for 2 hours at 37° C. During this incubation period a solution containing actinomycin D (Fluka) in complete MEM is set up. The final concentration of actinomycin D after addition to the wells is 1 μg/ml. At the end of the incubation period each antibody-TNF α or -TNF β mixture and 50 μl of actinomycin D are added to the wells of the microtiter plates. To some wells 100 μl of each dilution containing TNF α or TNF β alone are added. To some control wells only actinomycin D plus complete MEM is added. Thereafter the plates are incubated for 24 hours at 37° C.

At the end of this incubation period 20 μl of a thiazolyl blue solution (MTT, Calbiochem, 5 mg/ml in PBS) are added to each well. The plates are further incubated for 4 hours at 37° C. Then, supernatants are discarded, 200 μl of dimethylsulfoxide (DMSO, Farmitalia Carlo Erba) are added to each well and the extent of color development is read on a plate ELISA reader at 570 nm.

The OD values obtained for each antibody-TNF $\alpha$ or -TNF $\beta$ mixture are compared with those obtained for TNF $\alpha$ or TNF $\beta$ alone. The doses of TNF $\alpha$ or TNF $\beta$ giving, in the absence or presence of monoclonal antibody, OD values which are 50% of those obtained for the control wells (50% cytotoxicity) are determined. Monoclonal antibodies with the highest neutralizing activity are defined as those which determine the highest increase of the TNF $\alpha$ dose required to give 50% cytotoxicity.

6. Determination of the affinity of anti-TNF $\alpha$ monoclonal antibodies.

In order to determine the affinity of anti-TNF $\alpha$ monoclonal antibodies the following experiment is performed. 1 ng/ml ($6.25 \times 10^{-12}$M) of said monoclonal antibody or diluent alone (PBS supplemented with 0.5% BSA) are incubated with different concentrations of iodinated human TNF $\alpha$ (NEN, Wilmington, Del., concentrations ranging typically from $0.5 \times 10^{-11}$M to $4 \times 10^{-10}$M) in Eppendorff tubes for 4 hours at room temperature. At the end of the incubation period 1:5 diluted Immunobeads (170–5104, Bio-Rad, Segrate, Italy) are added to each tube and the tubes are further incubated for 1 hour. Then, the mixtures are centrifuged through a phthalate-dibutyl phthalate oil mixture (1:1.5 vol/vol, Fluka, AG). Immunobead-associated radioactivity is counted in a gammacounter. Data thus obtained are processed by means of an equilibrium binding data analysis program (EBDA, Elsevir Science Publishers, Amsterdam, Netherlands).

7. Determination of the dissociation rate constant ($k_{-1}$) of human TNF $\alpha$ bound to an anti-TNF $\alpha$ monoclonal antibody.

2 ng/ml ($1.25 \times 10^{-11}$M) of the monoclonal antibody produced by hybridoma 78 or buffer (PBS+0.5% BSA) alone are incubated with 2.5 ng/ml ($5 \times 10^{-11}$M) iodinated human TNF$\alpha$ for 4 hours at room temperature. Thereafter 1:5 diluted Immunobeads are added for 1 hour and the mixtures are then centrifuged twice. The resulting pellets are resuspended in 250 ng/ml ($5 \times 10^{-9}$M) "cold" human TNF $\alpha$ to compete for rebinding with any iodinated human TNF $\alpha$ that dissociates. After different times of incubation (see FIG. 5) at room temperature the pellets are centrifuged through an oil mixture as descibed in the previous section. Residual iodinated human TNF $\alpha$ specifically bound to the monoclonal antibody is then determined and the results are plotted as percentage radioactivity bound versus log time. The time for 50% dissociation (T ½) is read from this graph and used to calculate $k_{-1}$:

$$k_{-1} \frac{0.693}{T\frac{1}{2}}$$

8. Ouchterlony double immunodiffusion in agar.

In order to see if the monoclonal antibody produced by hybridoma 78 precipitates human TNF $\alpha$ a double diffusion assay is performed. For this purpose 1% agarose gel in 0.9% NaCl is used. The samples (human TNF $\alpha$ and the monoclonal antibody) are placed in circular wells. Patterns are allowed to develop for at least 24 hours at 4° C. before being photographed.

9. Determination of the FPLC size exclusion profiles of mixtures of human TNF $\alpha$ and an anti-TNF $\alpha$ monoclonal antibody.

For this purpose mixtures of human TNF $\alpha$ or iodinated human TNF $\alpha$ and purified anti-TNF $\alpha$ monoclonal antibody in human TNF $\alpha$ excess are set up (e.g. 100 $\mu$g/ml human TNF $\alpha$ and 30 $\mu$g/ml of monoclonal antibody or 5 ng/ml iodinated human TNF $\alpha$ and 2 ng/ml of monoclonal antibody) in PBS (for mixtures of 100 $\mu$g/ml human TNF $\alpha$ and 30 $\mu$g/ml of the monoclonal antibody) or in PBS+0.5% BSA (for mixtures of 5 ng/ml iodinated human TNF $\alpha$ and 2 ng/ml of monoclonal antibody). The mixtures are allowed to incubate for 4 hours at room temperature. Thereafter the mixtures, TNF $\alpha$ alone or the monoclonal antibody alone are chromatographed on a $10 \times 300$ mm Superose 6 FPLC column (Pharmacia LKB Biotechnology, Uppsala, Sweden) to generate $A_{280}$ absorbance profiles. The column is preequilibrated and eluted with 50 mM sodium phosphate, 150 mM NaCl, pH 7,2 buffer. Molecular weight standards are, typically, blue dextran (mw $2 \times 10^6$), human IgM (mw 900000), bovine thyroglobulin (mw 670000), bovine IgG (mw 158000), chicken ovalbumin (mw 44000), horse myoglobin (mw 17000), vitamin B12 (mw 1350).

10. Determination of the neutralizing activity in vivo of anti-TNF $\alpha$ monoclonal antibodies.

In order to evaluate the neutralizing activity in vivo of anti-TNF $\alpha$ monoclonal antibodies a model system for human TNF $\alpha$-induced lethal shock in mice is set up. For this purpose mice are injected intraperitoneally with different doses of human TNF $\alpha$ (typically 0.1 $\mu$g or 1 $\mu$g/mouse diluted in 0.25 ml PBS) and D-galactosamine (typically 36 mg/mouse diluted in 0.25 ml PBS). Mice injected with lethal doses of human TNF $\alpha$ die within 24–48 hours.

The neutralizing activity in vivo of the anti-TNF $\alpha$ monoclonal antibody is evaluated injecting mice intravenously with different doses of the monoclonal antibody (diluted in 0.25 ml PBS) and 90 minutes later intraperitoneally with a lethal dose of human TNF $\alpha$.

In another set of experiments the neutralizing activity in vivo of the anti-TNF $\alpha$ monoclonal antibody over time is evaluated. For this purpose the monoclonal antibody is administered at different times before and after the administration of a lethal dose of human TNF $\alpha$.

TABLE 1

Parameters of the binding of huTNF$\alpha$ to mAb78

| Measured affinity constant $K_{obs}$ ($\times 10^{-10}$M$^{-1}$) | Maximal binding capacity $B_{max}$ ($\times 10^{12}$M) | Ratio $B_{max}$/mAb78 |
|---|---|---|
| 3.16 ± 0.7* | 4.34 ± 0.46 | 0.71 ± 0.11 |

*Results (± SD) were obtained in 3 independent experiments.

TABLE 2

Concentrations of huTNF$\alpha$ giving 50% cytotoxicity on LM cells in the absence or presence of different concentrations of mAb78.

| Concentration of mAb78 | Concentration of huTNF$\alpha$ giving 50% cytotoxicity* | Neutralization Ratio+ |
|---|---|---|
| — | 3.3 ± 0.4 × 10$^{-12}$2M | — |
| 6.25 × 10$^{-9}$M | 4.6 ± 0.2 × 10$^{-9}$M | 1.36 |
| 6.25 × 10$^{-10}$M | 5.2 ± 0.5 × 10$^{10}$M | 1.21 |
| 6.25 × 10$^{-11}$M | 3.8 ± 1 × 10$^{-11}$M | 1.8 |

*Results (± SD) wete obtained in at least 3 independent experiments
+Neutralization Ratio = Ratio between concentration of mAb78 and concentration of neutralized huTNF$\alpha$.

TABLE 3

Lethality of mice treated with human recombinant TNF α and D-galactosamine.

| Dose of D-galactosamine[a] | Dose of TNF α[a] | Lethality |
|---|---|---|
| 36 mg/mouse | — | 0/4 |
| " | 0.01 μg/mouse | 2/4 |
| " | 0.1 μg/mouse | 4/4 |
| " | 1 μg/mouse | 4/4 |

[a]D-galactosamine and TNF α were coadministered intraperitoneally.

TABLE 4

Effect of monoclonal antibody 78 (mAb 78) on mice treated with human recombinant TNF α and D-galactosamine.

| Dose of D-galactosamine[a] | Dose of TNF α[a] | Dose of mAb78[b] | Lethality |
|---|---|---|---|
| 36 mg/mouse | 0.1 μg/mouse | — | 19/21 |
| 36 mg/mouse | 0.1 μg/mouse | 0.5 μg/mouse | 0/5 |
| 36 mg/mouse | 0.1 μg/mouse | 0.4 μg/mouse | 0/5 |
| 36 mg/mouse | 0.1 μg/mouse | 0.3 μg/mouse | 4/13 |
| 36 mg/mouse | 0.1 μg/mouse | 0.2 μg/mouse | 4/13 |
| 36 mg/mouse | 0.1 μg/mouse | 0.1 μg/mouse | 3/5 |
| 36 mg/mouse | 1 μg/mouse | — | 12/12 |
| 36 mg/mouse | 1 μg/mouse | 5 μg/mouse | 0/12 |
| 36 mg/mouse | 1 μg/mouse | 4 μg/mouse | 0/8 |
| 36 mg/mouse | 1 μg/mouse | 3 μg/mouse | 1/8 |
| 36 mg/mouse | 1 μg/mouse | 2 μg/mouse | 4/8 |
| 36 mg/mouse | 1 μg/mouse | 1 μg/mouse | 6/8 |

[a]See Table 1
[b]mAb was administered intravenously 1 h 30' before TNF α and D-galactosamine.

TABLE 5

Effect of monoclonal antibody 78 (MAb7B) administered at different times to mice treated with human TNF α and D-galactosamine.

| | Time of mAb78 and/or TNF α[a] administration | | | | | | | |
|---|---|---|---|---|---|---|---|---|
| −1 h 30' | 0 | +20' | +40' | +1 h | +2 h | +3 h | | Lethality |
| 10 μg 78 | 1 μg TNF | | | | | | | 31/33 |
| | 1 μg TNF | | | | | | | 1/24 |
| | 1 μg TNF + 10 μg 78 | | | | | | | 0/19 |
| | | | | | | | | 5/15 |
| | 1 μg TNF | 10 μg 78 | | | | | | 13/15 |
| | 1 μg TNF | | 10 μg 78 | | | | | 15/19 |
| | 1 μg TNF | | | 10 μg 78 | | | | 11/14 |
| | 1 μg TNF | | | | 10 μg 78 | | | 8/9 |
| | 0.1 μg TNF | | | | | | | 15/15 |
| 1 μg 78 | 0.1 μg TNF | | | | | | | 0/5 |
| | 0.1 μg TNF + 1 μg 78 | | | | | | | 0/10 |
| | 0.1 μg TNF | 1 μg 78 | | | | | | 0/5 |
| | 0.1 μg TNF | | 1 μg 78 | | | | | 0/5 |
| | 0.1 μg TNF | | | 1 μg 78 | | | | 3/15 |
| | 0.1 μg TNF | | | | 1 μg 78 | | | 2/10 |
| | 0.1 μg TNF | | | | | 1 μg 78 | | 5/5 |

[a]TNF was administered intraperitoneally together with 36 mg D-galactosamine/mouse, mAb 78 was administered intravenously.

what is claimed is:

1. A monoclonal antibody which is able to neutralize human Tumor Necrosis Factor (TNF) α, which is able to bind to and precipitate human Tumor Necrosis Factor α to form high molecular weight antigen-antibody complexes, and which is able to neutralize human Tumor Necrosis Factor β, wherein said antibody is produced by the hybridoma cell line 78 which is deposited under accession number ECACC 90110707.

2. A monoclonal antibody according to claim 1, wherein the smallest antigen-antibody complexes formed with human TNF α contain about two molecules of said antibody and about one human TNF α molecule and have molecular weight of about 400 kD as measured by gel filtration.

3. A monoclonal antibody according to claim 1 wherein said monoclonal antibody neutralizes trimer human TNF α in vitro at a molar ratio which is about 1.3:1.

4. Hybridoma cell line 78 which is deposited under accession number ECACC 90110707 and progeny thereof.

5. A monoclonal antibody secreted from the hybridoma cell line according to claim 4, or a antigen binding fragment of said antibody.

* * * * *